United States Patent
Oray et al.

(10) Patent No.: US 7,144,588 B2
(45) Date of Patent: Dec. 5, 2006

(54) METHOD OF PREVENTING SURGICAL ADHESIONS

(75) Inventors: B. Nicholas Oray, Woodbury, MN (US); Daniel Mooradian, Eagan, MN (US)

(73) Assignee: Synovis Life Technologies, Inc., St. Paul, MN (US)

( * ) Notice: Subject to any disclaimer, the term of this patent is extended or adjusted under 35 U.S.C. 154(b) by 533 days.

(21) Appl. No.: 10/346,240

(22) Filed: Jan. 17, 2003

(65) Prior Publication Data

US 2004/0141956 A1 Jul. 22, 2004

(51) Int. Cl.
*A61K 35/38* (2006.01)
*A61K 35/44* (2006.01)

(52) U.S. Cl. ............... 424/551; 424/569; 424/548; 424/543; 424/572; 424/570

(58) Field of Classification Search ............... 424/551, 424/572, 570, 548, 543, 569; 623/23.72, 623/23.73, 23.76, 1.41
See application file for complete search history.

(56) References Cited

U.S. PATENT DOCUMENTS

| | | | |
|---|---|---|---|
| 3,991,184 A | 11/1976 | Kludas et al. | 424/177 |
| 4,915,113 A | 4/1990 | Holman | 128/691 |
| 5,085,629 A | 2/1992 | Goldberg et al. | 604/8 |
| 5,306,286 A | 4/1994 | Stack et al. | 606/198 |
| 5,376,112 A | 12/1994 | Duran | 623/2 |
| 5,411,965 A | 5/1995 | Reid et al. | 514/279 |
| 5,413,798 A | 5/1995 | Scholl et al. | 424/715 |
| 5,447,922 A | 9/1995 | Lawrence et al. | 514/129 |
| 5,503,638 A | 4/1996 | Cooper et al. | 623/11 |
| 5,549,628 A | 8/1996 | Cooper et al. | 606/220 |
| 5,575,803 A | 11/1996 | Cooper et al. | 606/151 |
| 5,783,214 A | 7/1998 | Royer | 424/499 |
| 5,830,915 A | 11/1998 | Pikul et al. | 514/620 |
| 5,837,278 A | 11/1998 | Geistlich et al. | 424/444 |
| 5,837,533 A | 11/1998 | Boutin | 435/320.1 |
| 5,895,420 A | 4/1999 | Mirsch, II et al. | 623/2 |
| 6,187,048 B1 | 2/2001 | Milner et al. | 623/17.12 |
| 6,312,474 B1 | 11/2001 | Francis et al. | 623/23.72 |

FOREIGN PATENT DOCUMENTS

EP 0 897 942 A1 2/1999
WO WO 99/48540 9/1999

OTHER PUBLICATIONS

Merriam-Webster Online Dictionary, "prevent", http://m-w.com/cgi-bin/dictionary?book=Dictionary&va=prevent&x=12&y=17.*
Tu, R. et al. "Fixation of Bioprosthetic Tissues With Monofunctional and Multifunctional Polyepoxy Compounds", *Journal of Biomedical Materials Research* vol. 28, pp. 677-684 (1994).
Sung, H. W. et al. "Effects of Various Chemical Sterilization Methods on the Crosslinking and Enzymatic Degradation Characteristics of an Epoxy-Fixed Biological Tissue" *Journal of Biomedical Materials Res.* 37:376-383 (1997).
Sung, H.W. et al. "In Vitro Study of Enzymatic Degradation of Biological Tissues Fixed by Glutaraldehyde or Epoxy Compound" *Journal of Biomater. Sci. Polymer Edn.* vol. 8 No. 8 pp. 587-600 (1997).
Gratzer, P.F. et al. "Solvent Environment Modulates Effects of Glutaraldehyde Crosslinking on Tissue-Derived Biomaterials" *Journal of Biomedical Materials Research* vol. 31 pp. 533-543 (1996).
Hansbrough, J.F. et al. "Composite Grafts of Human Keratinocytes Grown on a Polyglactin Mesh-Cultured Fibroblast Dermal Substitute Function as a Bilayer Skin Replacement in Full-Thickness Wounds on Athymic Mice" *Journal of Burn Care & Rehabilitation* Sep./Oct. (1993) pp. 485-494.
N.A. Ashammakhi "Neomembranes: A Concept Review with Special Reference to Self-Reinforced Polyglycolide Membranes" *Journal of Biomedical Materials Research* vol. 33, pp. 297-303 (1996).
diZerega, Gere "Contemporary Adhesion Prevention" [online], *Center for Endometriosis Care Newsletter—Adhesions* Newsletter 1999 [retrieved on Jan. 17, 2003] Retrieved from http://www.centerforendo.com/news/adhesions/adhesions.htm.
"Seprafilm™ Products Brochure", Genzyme Corp. (2000) [retrieved on Jan. 17, 2003] Retrieved from http://www.genzymebiosurgery.com.
"Adcon® Products Brochure" Gliatech, Inc. (1998) [retrieved on Jan. 17, 2003] Retrieved from http://www.gliatech.com/pages/products/index.html.

* cited by examiner

*Primary Examiner*—Jean C. Witz
(74) *Attorney, Agent, or Firm*—Fredrikson & Byron PA

(57) ABSTRACT

The present invention relates to a method and composition for preventing surgical adhesions during surgery. Tissue surfaces and/or surgical articles involved in the surgery are separated by a biomaterial provided in the form of a non-crosslinked, decellularized and purified mammalian tissue (e.g. bovine pericardium). The biomaterial effectively inhibits fibrosis, scar formation, and surgical adhesions, while also serving as a scaffold for recellularization of the tissue site.

14 Claims, No Drawings

METHOD OF PREVENTING SURGICAL ADHESIONS

TECHNICAL FIELD

The present invention relates to method and compositions for preventing surgical adhesions during surgery.

BACKGROUND OF THE INVENTION

Adhesions, typically brought about by the formation of internal scar tissue, are one of the leading causes of post surgical complications. They are formed as a result of the body's natural response to the trauma of surgery. Body tissue repairs itself naturally following any incision, cauterization, suturing or other means of trauma. Adhesions typically form when two or more surfaces, such as the surfaces of discrete tissues, stick together at the site of surgery during the natural healing process. Adhesions can occur following virtually all types of surgeries and even the most careful and skilled surgeons find it difficult to avoid the formation of adhesions.

For a variety of reasons, adhesions occur in a very high percentage of patients after surgeries such as abdominal and pelvic surgery, and are particularly problematic there. Adhesions present a particular problem at places in the body where a surgeon cuts or handles tissues that normally should remain separate. Such tissues will sometimes become stuck together, causing fibrous scar tissue to form. When this happens, surgical complications result. The most common complications include bowel obstruction, female infertility, and chronic debilitating pain. In addition to pain and bodily complications, adhesions lead to increased medical expenses. Costs include subsequent surgeries to remove or separate adhesions, doctor visits, pain medication and compensation for lost work time. Also, if a patient were to have a subsequent operation in the same surgical site, such operation can be complicated by existing adhesions. Surgeons have to spend a considerable amount of time removing the adhesions before a new procedure can begin. This may also prolong the patient's recovery time and increases the risk and cost of the surgery.

Therefore, prevention of adhesions is an important goal of surgical practice. Many approaches to prevent adhesions have been suggested, but they either have not generally withstood rigorous clinical examination or they have major practical limitations. One such approach is to perform an operation to remove the adhesions. In the United States, several procedures are performed annually to remove adhesions. However, many times these operations are not effective because the adhesions simply reform.

Another approach to preventing adhesions involves the use of agents such as anti-inflammatory agents, non-steroidal anti-inflammatory drugs, anticoagulants, and fibrinolytic agents to reduce the inflammatory response during surgery. Anti-inflammatory agents would be helpful if used in large doses, but since large doses can have negative effects on other organs (immunosuppression and delayed wound healing), the positive benefits of preventing adhesions tend to be outweighed by the other negative effects. Moreover, the reports of their results in reducing adhesions have not been encouraging. See Gere diZerega, MD, "Contemporary Adhesion Prevention", Center for Endometriosis Care Newsletter, Copyright 1999 (see www.centerforendo.com/news/adhesions/adhesions.htm).

One new advance in the field of adhesion prevention is the development of barriers to be used in surgical procedures. One type of a barrier includes liquid solutions that are placed on the sites of surgery with the aim of separating tissue at risk surfaces. One example of a liquid barrier includes Gliatech's ADCON® products, which are provided in the form of resorbable gels and solutions designed to inhibit adhesions. The ADCON® products are applied directly to the surgical site. The gels and solutions are themselves resorbed by the body within approximately four weeks, and therefore, do not require surgical removal. See the ADCON® products brochure, Gliatech, Inc., 1998. One problem with liquid barriers, however, is that they tend to be absorbed too rapidly, so their duration of action is not sufficient to cover the period during which adhesives are most likely to form.

Another example of a barrier to be used in adhesion prevention is a structural barrier such as a sheet of material, which is introduced between layers of traumatized tissue during surgery. An ideal structural barrier preferably persists during the first critical stages of healing, has no effect on wound healing, is bioresorbable, and does not promote bacterial growth.

One well-known structural barrier product that has been developed to prevent adhesion formation is provided under the tradename Seprafilm™, manufactured by Genzyme Corporation. Seprafilm™ products are transparent films that are designed to act as a temporary barrier between two tissue layers during the early days of wound healing, thereby reducing adhesion formation. More specifically, Seprafilm™ products are sterile bioresorbable transparent adhesion barriers composed of two anionic polysaccharides, namely sodium hyaluronate and carboxymethylcellulose. Together, these two biopolymers are chemically modified with an activating agent 1-(3-dimethylaminopropyl)-3-ethylcarbodimide hydrochloride. Seprafilm™ products hydrate to a gel within 24–48 hours following placement in the body and then slowly resorb from the abdominal cavity in about five days. They are excreted from the body within 28 days. See the Seprafilm™ products brochure, Genzyme Corporation, 2000.

When used, Seprafilm™ products are placed at a desired site within the body, with that desired site being as dry as possible. Before placing Seprafilm™ products in the body, the site of application is thoroughly aspirated of excess fluid. The Seprafilm™ products are kept in their package until immediately before use. In one form, for example, the film measures 5 inches by 6 inches, though it can also be cut with scissors to achieve a desired size and shape. When applying, the surgeon avoids contact with any tissue surfaces until directly at the site of application. If contact does occur, moderate application of standard irrigation solution is used to gently dislodge the film from the unintended tissue surface. Once at the proper site of application, the biomaterial is adhered to the tissue by gently pressing the biomaterial down with a dry glove or instrument. The biomaterial remains at the site of application until it dissolves into a gel. See the Seprafilm™ products brochure, Genzyme Corporation, 2000.

While Seprafilm™ products and others have provided several advantages in this field, they still suffer several drawbacks. The primary drawback is that, while they do reduce the occurrence of adhesions, the amount reduced is less than ideal. For example, Genzyme reports that clinical findings have shown that when used in abdominal procedures, Seprafilm™ products have prevented adhesions in 51% of patients, and that only 15% of patients treated with Seprafilm™ products had dense adhesions. While the prevention of adhesions by 51% is helpful, it is still less than ideal. Hence, there remains a need for an improved composition and method for reducing surgical adhesions, and particularly compositions that will provide an optimal combination of ease of use, adhesion reduction, and applicability to a variety of surgical situations. The present invention addresses this need.

SUMMARY OF THE INVENTION

The present invention is directed to a method and composition for reducing adhesion formation in the body following a surgical procedure, using a remodelable implantable biomaterial comprising a sterile, non-crosslinked, decellularized and purified mammalian tissue, and preferably one having a major percentage of its available amine groups alkylated. A particularly preferred biomaterial of the present invention is described in Applicant's own U.S. Pat. No. 6,312,474, the disclosure of which is herein incorporated by reference. Applicants have discovered that a biomaterial prepared in the manner described in the '474 patent reduces the incidence of adhesions when used to separate tissue surfaces following surgery.

Furthermore, the preferred biomaterial provides the added benefit of being "remodelable", in the sense that it can serve as the scaffold for recellularization of the tissue site and hence, is incorporated structurally into the host. It thereby provides mechanical stability to the host as compared, for instance, to the use of a liquid or gel barrier. If permitted to remain in the body over time, cells of the surrounding host tissue are able to infiltrate the biomaterial and repopulate its surface with host cells. The use of biomaterial that is remodelable in this manner is unique, particularly as compared to tissue barriers known in the art, since it is neither temporary nor permanent, in the conventional sense. As used herein with respect to this biomaterial, the word "remodel" and inflections thereof will refer to a material that, once implanted in vivo, is adapted to be both absorbed by the body over time, while also serving as a scaffold for recellularization of the tissue site.

The invention further provides a composition and related method of preventing post-operative surgical adhesions between abutting surfaces, the method comprising the steps of providing a biomaterial as described herein and positioning the biomaterial between the abutting surfaces in the course of surgery. The positioned biomaterial serves as a remodelable barrier that keeps tissue surfaces separated during the early days of wound healing after surgery, while also serving as a scaffold for the longer-term recellularization of the tissue site. The method can be used for any suitable surgery in which adhesions pose a risk. The abutting surfaces, in turn, can be selected from the group consisting of two or more surface portions of the same tissue and/or surfaces from each of two or more discrete tissues, and/or the surfaces of a tissue and implanted material. The meaning of the word "tissue" as used in this application should be construed broadly to cover any part or organ of the body.

DETAILED DESCRIPTION

The preferred biomaterial of this invention comprises a non-crosslinked, decellurized and purified mammalian tissue having a major percentage of its available amine groups alkylated. The tissue can be obtained from any suitable source, particularly including mammalian sources, e.g., in the form of collagenous connective tissue with three-dimensional intertwined fibers. In turn, the material has preferably been alkylated by the use of an alkylating agent selected from the group consisting of 1,2-epoxy-R compounds where R is an alkyl group up to 6 carbon atoms. Preferred alkylating agents include propylene oxide and methyl glycidyl ether.

Such tissues generally include serous and fibro-serous membranes. In a particularly preferred embodiment, the tissue source is selected from pericardium, peritoneum, fascia lata, dura mater, dermis, and small intestinal submucosa. In a further preferred embodiment, the tissue is bovine pericardium.

Biomaterials of the present invention can be prepared, treated, tested and packaged according to methods substantially similar to the methods described in Applicant's own U.S. Pat. No. 6,312,474 which has been incorporated by reference. Such a biomaterial can be provided in any suitable form, and can be adapted for use in a variety of surgical applications. In one embodiment, the biomaterial is packaged in one or more generic sizes, to be selected and trimmed by the surgeon to a desired size and shape. In an alternative embodiment, the biomaterial is packaged in a plurality of sizes and/or shapes, and is preferably also labeled for a particular type of surgery so the surgeon does not need to further trim it. For example, the biomaterial can be provided in the form of flat or textured (e.g., rippled, corrugated, roughened) sheets or strips. The biomaterial can be packaged using conventional means, such that the tissue and package contents remain sterile and non-pyrogenic as long as the package is not opened and/or damaged. Preferably, the biomaterial is kept in a packaged, dry location.

The preferred method of this invention comprises the steps of providing a biomaterial as described herein and positioning it between abutting surfaces in the course of surgery. The biomaterial is positioned into place between abutting surfaces by any suitable means. Usually, the biomaterial is placed in a manner that it separates the tissues of the body that have been traumatized by surgery from remaining healthier tissues of the body. Alternatively, the biomaterial is placed in a manner that it separates two traumatized tissues of the body. In these and other embodiments, separation in this manner reduces the formation of adhesions between tissue surfaces.

Once the biomaterial is properly positioned at the desired site, the surgeon can extend it beyond the incision or traumatized area to facilitate its coverage around the tissue contours. The biomaterial is then allowed to contact and thereby be held in position within the desired site (for example, held by surface tension). The biomaterial conforms well to moist tissues and can be used in the presence of blood. Alternatively, the biomaterial may be sutured and/or stapled into place, or retained using any other suitable materials (such as adhesives) or methods. The surgical site is then closed according to the standard technique of the surgeon. The biomaterial requires no modification of a surgical technique and does not negatively affect wound healing.

While it should be noted that this biomaterial may be used for any type of surgery in order to prevent the formation of adhesions, it is especially useful for surgeries selected from peritoneal, pericardial, obstetric, gynecological, neurosurgical, arthroscopic, orthopedic, plastic, reconstructive, muscle, or tendon surgery.

The present invention will be further described with reference to the following non-limiting examples. It will be apparent to those skilled in the art that changes can be made in the embodiments described without departing from the scope of the present invention.

EXAMPLE 1

A study was conducted to assess the use of the above biomaterial as an anti-adhesion barrier for preventing abdominal or pelvic adhesions, as well as its remodeling and anti-inflammatory properties. As seen below, the biomaterial provides an optimal combination of anti-adhesion, anti-inflammatory, and remodeling properties.

The biomaterial was prepared for this study using the general methods described in Applicant's own U.S. Pat. No. 6,312,474. The biomaterial was also sized and shaped to flat sheets having the dimensions of 6 cm×8 cm and each were sterilized by conventional e-beam methods.

A unilateral hysterectomy surgery was performed on adult female rabbits having a weight of between 2.5–4.5 kg. A total of five (5) animals underwent hysterectomy without implantation of the biomaterial and served as controls. In an additional ten (10) animals, the biomaterial was positioned over the hysterectomy site and was held in place by a suture placed at each end. In all cases, the abdomen was closed and the animals were monitored for a period of 14, 15, or 29 days as indicated in Table 1 below. There were no post-operative complications in any of the animals used in this study. After the period of 14, 15, or 29 days, the hysterectomy site was reopened and assessed. After assessment, the site was explanted from the animal and further processed for histological analysis, for example by using H&E staining. The bulk of the implants were retrieved after 14 or 15 days but two (2) were left in place for 29 days in order to collect information regarding the biomaterial's remodeling at the one-month time point.

The primary purpose of this study was to confirm the use of the biomaterial as an anti-adhesive barrier. In order to make this determination, on either the $14^{th}$, $15^{th}$ or $29^{th}$ day, the hysterectomy site was reopened and an assessment was made of the locations and severity of adhesions in each animal. A digital video record of this assessment was also made. The adhesions seen were counted and scored in terms of severity according to the system established by the Adhesion Scoring Group, published in 1994. Adhesions were scored as follows: Grade 0=none, Grade 1=filmy, avascular adhesions, Grade 2=dense and/or vascular adhesions, and Grade 3=cohesive adhesions.

With regard to the five (5) control animals, adhesions were a predictable result of the hysterectomy surgery. As seen in Table 1, the control animals, when assessed after 14, 15, or 29 days, showed adhesions frequently of Grade 2 or 3 to the bowel, bladder, and uterus. In contrast, of the ten (10) animals undergoing hysterectomy followed by implantation of the biomaterial as an anti-adhesion barrier, only five (5) were observed to have adhesions after 15 or 29 days. Of these, only two showed adhesions of Grade 3 and one of these was peculiar in that the biomaterial was adhered directly to the peritoneal aspect of the abdominal incision. A sixth animal did exhibit a single adhesion to a portion of the uterine stump that had not been completely covered by the biomaterial at the time of implantation. Thus, it can be seen that the biomaterial is effective in preventing adhesions in hysterectomy surgery, especially those of the more severe type.

A second purpose of this study was to determine the extent to which the biomaterial may cause any inflammation in the surrounding host tissue. After adhesions in the hysterectomy site were assessed, the hysterectomy sites in the biomaterial treated animals were explanted. The explants included the biomaterial along with the attached adhesions when possible. The explants were then photographed. The photographs revealed that the biomaterial was clearly distinguishable from the surrounding host tissue. The photographs also revealed that the biomaterial/host interface was largely free of inflammation. In other words, the interface showed little or no swelling and redness. The host tissue also exhibited a generally smooth, firm appearance that was continuous with the appearance of the biomaterial itself. Also, no implant fragmentation or degradation was observed. This was consistent with the relative absence of inflammation at the biomaterial/host interface.

The explants were then quartered to expose the underlying hysterectomy site as well as the biomaterial in cross-section and later H&E stained. After doing so, the interface between the biomaterial and the host tissue was again quite clear. Evidence of host healing at the site of injury was also seen. Increased cellularity and vascularity were observed and these would be expected as a party of the normal healing response. Also, the number of acute (i.e. polymorphonuclear leukocytes) and/or chronic (monocytes, macrophages) inflammatory cells was relatively small. An occasional foreign body giant cell, generally associated with chronic inflammation, was observed and this may well have been related to the presence of the remnant suture material rather than with the biomaterial itself. Thus, it can be seen that the biomaterial does not trigger significant inflammatory responses in the host tissue.

A final purpose of this study was to assess the remodeling properties of the biomaterial. By itself and before implantation, the biomaterial of this invention is accellular and is generally composed of a mixture of amorphous and fibrillar collagen of limited porosity. It would appear that once implanted, the biomaterial allows the host tissue to repopulate its surface with more complex host cells. In order to determine this, sections of 14 and 15 day explants were stained with hematoxylin and eosin (H&E staining) and reviewed. The staining revealed that the surrounding host tissue (for example, fibroblasts and/or mesothelial cells) had repopulated the biomaterial surface. Importantly, each of the biomaterial surfaces appeared to have a complete (or nearly complete) covering of host cells that in some instances was a single layer thick.

This host cell repopulation was most pronounced at the lateral edges of the biomaterial where natural separation of the collagen bundles offered less resistance to cell migration. While it was not possible to identify these cells histologically, they were likely mesothelial cells that repopulated the surface of the biomaterial by direct migration from surrounding tissues. Also, mesothelial cells possess fibrinolytic properties similar to those of vascular endothelial cells and this may have contributed to the relative lack of adhesions observed on the biomaterial. This facet can be used to both explain, and enhance the use of the biomaterial for the purposes described herein.

Finally, two (2) of the biomaterial implants were left in place for 29 days in order to collect further information regarding the biomaterial's remodeling at a one-month time point. At this point, it was observed that the host tissue was separated by the acellular biomaterial by a transitional zone characterized by active remodeling of the biomaterial. In this zone, alternating bands of implant collagen (distinguishable by their relative acellularity) were interspersed with new host tissue. Implant angiogenesis (i.e. the development of new blood vessels within the implant itself) was a consistent finding in the 29 day implants (as well as in the 14 and 15 day implants). Thus, it can be deduced that the biomaterial of this invention had remodeling properties, especially after being left in the body for a longer period of time, for example 29 days.

The results from the above study suggest that the biomaterial of this invention possesses a unique combination of anti-adhesion, anti-inflammatory, and remodeling properties. With regard to the anti-adhesion properties, while the difference in the frequency of adhesion formation in the control and the biomaterial treated animals was not found to be statistically significant, there was nonetheless a clear trend in the data supporting the hypothesis that use of the biomaterial as a physical barrier in abdominal surgery can reduce the formation of adhesions. This was confirmed by an analysis that focused only on Grade 3 adhesions (i.e. cohesive adhesions), which are the most likely to be clinically relevant. The frequency of Grade 3 adhesions was significantly higher in the control group (100%) than in the group using the biomaterial (20%).

TABLE 1

ADHESION FORMATION FOLLOWING RABBIT HYSTERECTOMY IN CONTROL AND IN TISSUE-TREATED ANIMALS

| CONTROL | TIME | ADHESIONS | DESCRIPTION |
| --- | --- | --- | --- |
| USDA #B1 | 14 days | + | Adhesion of bladder "fat" to incision, and mesentery to stump of uterine horn (No Grade recorded) |
| USDA #B2 | 14 days | + | Adhesion of bladder fat to suture line, of bladder to uterine stump, and mesentery to uterine stump (all Grade 3) |
| USDA #39 | 29 days | + | Adhesion to small bowel (Grade 3), Adhesion to ovary (Grade 3), Adhesion to bladder (Grade 1) |
| USDA #47 | 15 days | + | Adhesion to small bowel (Grade 3), Adhesion to bladder serosa (Grade 2) |
| USDA #53 | 29 days | + | Adhesion to fat (minor), Adhesion to ovary (Grade 2) |
| Total | | 5/5 = 100% | |
| TREATED | | | |
| USDA #B3 | 14 days | − | Note: the implant did NOT completely cover the uterine stump. As a result, there was a small adhesion to the uncovered portion of the uterine stump. Implant was clear of adhesions. |
| USDA #B4 | 14 days | + | Adhesion of bladder to implant (Grade 3, bladder to mesentery (Grade 1) |
| USDA #41 | 15 days | + | Adhesion of implant to incision Grade 3 |
| USDA #41 | 15 days | − | |
| USDA #42 | 15 days | − | |
| USDA #48 | 15 days | − | |
| USDA #49 | 15 days | + | Adhesion to bladder serosa (no grade) |
| USDA #50 | 15 days | − | |
| USDA #51 | 29 days | + | Adhesion to bladder (Grade 1–2), Adhesion to secum (Grade 2), thin fibrous adhesion to large bowel |
| USDA #52 | 29 days | + | Adhesion to mesentery (Grade 2), small bowel adhesion to serosa (Grade 2) |
| Total | | 5/10 = 50% | |

The invention claimed is:

1. A method of reducing post-operative surgical adhesions between abutting surfaces, the method comprising the steps of providing a biomaterial comprising a sterile, non-crosslinked, decellularized and purified mammalian tissue having a major percentage of its available amine groups alkylated and positioning the biomaterial between the abutting surfaces in the course of surgery.

2. The method of claim 1 wherein the biomaterial is selected from the group consisting of serous and fibro-serous membranes.

3. The method of claim 2 wherein the biomaterial is selected from the group consisting of pericardium, peritoneum, fascia lata, dura mater, dermis, and small intestinal submucosa.

4. The method of claim 3 wherein the biomaterial comprises bovine pericardium.

5. The method of claim 1 wherein the biomaterial has been alkylated by an alkylating agent selected from the group consisting of 1,2-epoxy-R-compounds where R is an alkyl group up to 6 carbon atoms.

6. The method of claim 5 wherein the alkylating agent is propylene oxide.

7. The method of claim 5 wherein the alkylating agent is methyl glycidyl ether.

8. The method of claim 1 wherein the biomaterial is provided in the form of flat or textured sheets or strips.

9. The method of claim 1 wherein the surgery is selected from peritoneal, pericardial, obstetric, gynecological, neurosurgical, arthroscopic, orthopedic, plastic, reconstructive, muscle, or tendon surgery.

10. The method of claim 1 further including the step of suturing the biomaterial into place between the surfaces.

11. The method of claim 1 further including the step of stapling the biomaterial into place between the surfaces.

12. The method of claim 1 further including the step of allowing the biomaterial to adhere into place between the surfaces.

13. The method of claim 1 wherein the abutting surfaces are selected from the group consisting of two surface portions of the same tissue, surfaces from each of two or more discrete tissues, and the surfaces of a tissue and implanted material.

14. The method of claim 1 wherein the biomaterial is selected from the group consisting of serous and fibro-serous membranes, and wherein the biomaterial has been alkylated by an alkylating agent selected from the group consisting of 1,2-epoxy-R-compounds where R is an alkyl group up to 6 carbon atoms, and the surgery is selected from peritoneal, pericardial, obstetric, gynecological, neurosurgical, arthroscopic, orthopedic, plastic, reconstructive, muscle, or tendon surgery.

* * * * *